United States Patent [19]

Kurono et al.

[11] Patent Number: 5,036,080
[45] Date of Patent: Jul. 30, 1991

[54] (D)-6-FLUORO-2,3-DIHYDRO-2',5-DIOXO-SPIRO[4H-1-BENZOPYRAN-4,4'-IMIDAZOLIDE]-2-CARBOXAMIDE COMPOUNDS

[75] Inventors: Masayasu Kurono; Toshinao Usui; Kenji Miura; Yasuaki Kondo; Kiichi Sawai, all of Aichi, Japan

[73] Assignee: Sanwa Kagaku Kenyusho Co., Ltd., Aichi, Japan

[21] Appl. No.: 331,329

[22] Filed: Mar. 31, 1989

[30] Foreign Application Priority Data

Apr. 7, 1988 [JP] Japan ................................. 63-84098
Nov. 28, 1988 [JP] Japan ................................ 63-298220

[51] Int. Cl.$^5$ ................ A61K 31/415; C07D 491/107
[52] U.S. Cl. .................................... 514/333; 514/337; 514/389; 514/390; 546/256; 546/269; 548/309
[58] Field of Search ................ 548/309; 514/389, 390, 514/333, 337; 546/256, 269

[56] References Cited

U.S. PATENT DOCUMENTS

| | | | |
|---|---|---|---|
| 4,127,665 | 11/1978 | Sarges et al. | 548/309 X |
| 4,650,798 | 3/1987 | Minami et al. | 548/309 X |
| 4,780,472 | 10/1988 | Ueda et al. | 514/389 |

FOREIGN PATENT DOCUMENTS 63-57588 3/1988 Japan.
63-126881 5/1988 Japan.

OTHER PUBLICATIONS

March, J., Advanced Organic Chemistry, McGraw Hill. New York, 1968, pp. 672–673.

J. Kinoshita et al., *Jap. J. Opthalmol.* vol. 20, pp. 339–410, 1976.
K. Gabbay, *Int. Congr. Ser. Excerpta Med.,* vol. 403, p. 594, 1977.
M. Peterson et al., Metabolism, vol, 28, p. 456, 1979.

*Primary Examiner*—Joseph Paul Brust
*Attorney, Agent, or Firm*—Armstrong, Nikaido, Marmelstein, Kubovcik & Murray

[57] ABSTRACT

Hydantoin derivatives of the formula

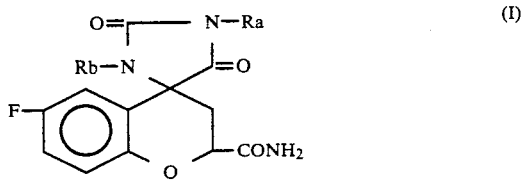

wherein Ra and Rb are same or different, each being hydrogen atom, alkanoyl, substituted or none-substituted aroyl, heteroaroyl, alkoxycarbonyl, substituted or none-substituted aralkoxycarbonyl, aryloxycarbonyl, N-alkylcarbamoyl, N,N-dialkylcarbamoyl, substituted or none-substituted N-aralkylcarbamoyl, alkoxyalkyl, 1-(acyloxy)-alkyl, alkylmercapto, substituted or none-substituted arylmercapto, alkylsulfinyl, substituted or none-substituted arylsulfinyl, alkylsulfonyl or substituted or none-substituted arylsulfonyl, but both of Ra and Rb do not concurrently mean hydrogen atom, a process for the preparation of the derivatives, and use thereof as an agent for preventing and curing chronic complications due to diabetes.

3 Claims, No Drawings

(D)-6-FLUORO-2,3-DIHYDRO-2',5-DIOXO-SPIRO[4H-1-BENZOPYRAN-4,4'-IMIDAZOLIDE]-2-CARBOXAMIDE COMPOUNDS

BACKGROUND OF THE INVENTION

1. Field of the Invention

The present invention relates to novel hydantion derivatives and more particularly (d)-6-fluoro-2,3-dihydro-2',5'-dioxo-spiro-[4H-1-benzopyran-4,4'-imidazolidine]-2-carboxamide derivative, a process for the preparation thereof, and use thereof as an agent for preventing and curing chronic complications due to diabetes.

2. Related Arts

Hitherto, various studies have been made for finding out an effective agent to cure diabetes, which can be orally administered. As a result, various agents therefor, each of which comprises as an effective ingredient, sulfonyl urea, mesooxalate or guanidine derivatives or the like have been developed and marketed but those are of a mere symptomatic treating agent to a hyperglycoplasmia due to the diabetes, specific chronic complications such as diabetic cataract, diabetic neuropathy, diabetic retinopathy and the like, but there is almost no effective agent for preventing and curing the complications and thus it may be said no effective therapeutic system has been established.

Therefore, various studies have also been made for developing an effective agent for preventing and curing such intractable diseases due to diabetes but it is the fact that there is almost no success case. As one of the studies, there is a search on inhibition substance to an aldose reductase, since the enzyme reduces in vivo of human and other animals, aldose such as glucose and galactose into corresponding polyols such as sorbitol and galactitol and it has been known that said complications will appear when the formed sorbitol and galactitol are accumulated at crystalline lens, peripheral nerve, kidney or the like in patients of diabetes or galactosemia ["Jap. J. Opthalmol.", Vol. 20, page 399 (1976); "Int. Congr. Ser. Excerpta Med.", Vol. 403, page 594 (1977); and "Metabolism", Vol. 28, page 456 (1979)].

Various compounds having the inhibition activity to the aldose reductase have hitherto been reported and the present inventors have also found that (d)-6-fluoro-2,3-dihydro-2',5'-dioxo-spiro[4H-1-benzopyran-4,4'-imidazolidine]-2-carboxamide of the following formula shows a remarkable activity of inhibition to the aldose reductase in vitro and vivo tests, in comparison with other agents [Jap. Pat. Nos. Sho 63-57588 (A) and 63-126881 (A) equivalent to U.S. Ser. No. 07/090729 filed Aug. 28, 1987 (now U.S. Pat. No. 4,861,792) and European Pat. Publn. No. 0264586 (A1)].

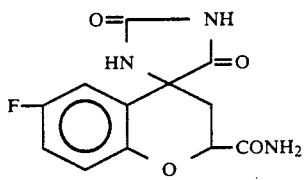

SUMMARY OF THE INVENTION

An principal object of the present invention lies in providing a novel compound having an inhibition ability to aldose reductase, which is rapidly absorbed in a tissue containing the aldose reductase to develop its activity therein, whereby an accumulation of sorbitol and galactitol is inhibited to make possible a treatment of complications due to diabetes.

Another object of the invention is to provide a process for the preparation of such a compouns.

A still other object of the invention is to provide a pharmaceutical composition which comprises such a compound, as an effective ingredient.

According to the invention, the principal object can be attained by a (d)-6-fluoro-2,3-dihydro-2',5'-dioxo-spiro[4H-1-benzopyran-4,4'-imidazolidine]-2-carboxamide derivative of the formula

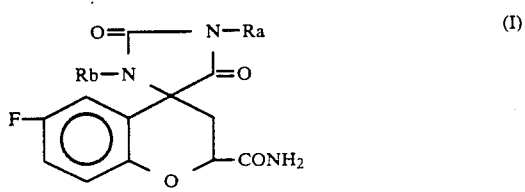

wherein Ra and Rb are same or different, each being hydrogen atom, alkanoyl, substituted or none-substituted aroyl, heteroaroyl, alkoxycarbonyl, substituted or none-substituted aralkoxycarbonyl, aryloxycarbonyl, N-alkylcarbamoyl, N,N-dialkylcarbamoyl, substituted or none-substituted N-aralkylcarbamoyl, alkoxyalkyl, 1-(acyloxy)alkyl, alkylmercapto, substituted or none-substituted arylmercapto, alkylsulfinyl, substituted or none-substituted arylsulfinyl, alkylsulfonyl or substituted or none-substituted arylsulfonyl, but both of Ra and Rb do not concurrently mean hydrogen atom.

The compounds (I) show a powerful inhibition activity to aldose reductase in vivo but, in general, its activity is not so high in vitro test and thus it shall be estimated that the substituents Ra and Rb are decomposed or removed in living body to develop the activity. The substituents Ra and Rb decomposable in vivo have functions of leading the compound (I) in to a living tissue where the aldose reductase presents, and of converting the compound (I) into a form showing an inhibition activity to the aldose reductase, and thus are quite important in making the compound (I) into a so-called as "Pro-drug".

Various radicals may be listed as substituents for symbols Ra and Rb, other than hydrogen, as shown in following items.

(i) An acyl group inclusive of alkanoyl group (especially alkanoyl group having 1 to 10 carbon atoms), substituted or none-substituted aroyl group (especially benzoyl radical which may be substituted), heteroaroyl group, alkoxycarbonyl group (especially alkoxycarbonyl group having 1 to 10 carbon atoms), substituted or none-substituted aralkoxycarbonyl group (especially benzyloxycarbonyl radical which may be substituted), aryloxycarbonyl group (especially phenoxycarbonyl radical which may be substituted); for instance acetyl, propionyl, pivaloyl, cyclohexylacetyl, phenylacetyl, benzoyl, chlorobenzoyl, methoxybenzoyl, methylbenzoyl, furoyl, nicotinoyl, methoxycarbonyl, ethoxycarbonyl, cyclohexyloxycarbonyl, benzyloxycarbonyl, phenoxycarbonyl, chlorophenoxycarbonyl, methoxyphenylcarbonyl and methylphenylcarbonyl radicals:

(ii) A carbamoyl group inclusive of N-alkylcarbamoyl group (especially N-alkylcarbamoyl group having 1 to 10 carbon atoms), N,N-dialkylcarbamoyl group (especially N,N-dialkylcarbamoyl group having 1 to 10 carbon atoms), N-arylcarbamoyl group (especially N-phenylcarbamoyl radical which may be substituted), substituted or none-substituted N-aralkylcarbamoyl group (especially N-benzylcarbamoyl radical which may be substituted); for instance N-methylcarbamoyl, N-ethylcarbamoyl, N-cyclohexylcarbamoyl, N,N-diethylcarbamoyl, N-benzylcarbamoyl, N-chlorobenzylcarbamoyl, N-methoxybenzylcarbamoyl, N-phenylcarbamoyl, N-chlorophenylcarbamoyl, N-methoxyphenylcarbamoyl and N-methylphenylcarbamoyl radicals:

(iii) An alkoxyalkyl group (especially $C_1$-$C_{10}$-alkoxy-$C_1$-$C_6$ alkyl) and 1-(acyloxy)alkyl group [especially 1-(acyloxy)-$C_1$-$C_6$ alkyl]; for instance, methoxymethyl, ethoxymethyl, methoxyethyl, ethoxyethyl, acetyloxymethyl, pivaloyloxymethyl and benzoyloxymethyl radicals:

(iv) A mercapto group or oxidized form thereof, inclusive of alkylmercapto group (especially alkylmercapto group having 1 to 10 carbon atoms), substituted or none-substituted arylmercapto group (especially phenylmercapto radical which may be substituted), alkylsulfinyl group (especially alkylsulfinyl group having 1 to 10 carbon atoms), substituted or none-substituted arylsulfinyl group (especially phenylsulfinyl radical which may be substituted), alkylsulfonyl group (especially alkylsulfonyl group having 1 to 10 carbon atoms) and substituted or none-substituted arylsulfonyl group (especially phenylsulfonyl radical which may be substituted); for instance, methylmercapto, ethylmercapto, benzylmercapto, phenylmercapto, methylsulfinyl, ethylsulfinyl, benzylsulfinyl, phenylsulfinyl, methylsulfonyl, ethylsulfonyl, benzylsulfonyl, phenylsulfonyl and methylphenylsulfonyl radicals.

The derivatives (I) according to the present invention can be prepared in a general manner to be applied for the preparation of compounds analogous in structure. Some processes for preparing the derivatives shall be shown below, in which Ra and Rb in chemical formulae have the meanings as referred to.

a) The derivative (I), wherein the substituents Ra and Rb are radicals other than carbamoyl, can be prepared by reacting a compound of the formula

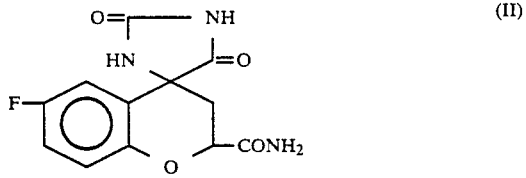

with a compound of the formula

Rc—X wherein Rc is hydrogen atom, alkanoyl, substituted or none-substituted aroyl, heteroaroyl, alkoxycarbonyl, substituted or none-substituted aralkoxycarbonyl, alkoxyalkyl, 1-(acyloxy)alkyl, alkylmercapto, substituted or none-substituted phenylmercapto, alkylsulfinyl, substituted or none-substituted phenylsulfinyl, alkylsulfonyl, substituted or none-substituted phenylsulfonyl, and X is a removable radical.

Followings may be listed as the compound Rc-X preferable for introducing the radical of Rc. Alkanoyl halides having 1 to 10 carbon atoms such as chloride or bromide of acetyl, propionyl, pivaloyl, cyclohexylacetyl and phenylacetyl; alkaneanhydrides having 2 to 10 carbon atoms such as acetic anhydride or propionic anhydride; aroyl halides such as chloride or bromide of benzoyl, chlorobenzoyl, methoxybenzoyl and methylbenzoyl; heteroaroyl halides such as chloride or bromide of furoyl or nicotinoyl; alkylchloroformates such as methylchloroformate, ethylchloroformate and cyclohexylchloroformate; arylchloroformates such as phenylchloroformate; alkoxyalkyl halides such as chloride or bromide of methoxymethyl and ethoxymethyl; 1-(acyloxy)-$C_1$-$C_6$ alkyl halides such as chloride or bromide of pivaloyloxymethyl and benzoyloxymethyl; arylsulfenyl halides such as chloride or bromide of phenylsulfenyl; alkylsulfonyl halides such as chloride or bromide of methanesulfonyl; arylsulfonyl halides such as toluenesulfonylchloride.

The reaction can be carried out under conditions for conventional N-acylation and N-alkylation, for instance in the presence of potassium carbonate, potassium hydroxide, sodium hydroxide or the like inorganic base; triethylamine, pyridine or the like inert organic base; or with use of sodium or potassium salt of the compound (II), in a suitable solvent such as dimethylsulfoxide, N,N-dimethylformamide, 1,2-dimethoxyethane or pyridine, and at a temperature of $-30$ to $100°$ C.

When the sodium or potassium salt of the compound (II) is to be selected for the starting material, the salt will be formed in situ by adding sodium or potassium hydride, in case of that anhydrous solvent such as dimethylsulfoxide, N,N-dimethylformamide or pyridine is selected and setting the temperature condition at $0°$–$30°$ C., for said reaction.

(b) The derivative (I), wherein the substituents Ra and Rb are carbamoyl groups, can be prepared by reacting the compound (II) with isocyanate of the formula Rd-NCO wherein Rd is hydrogen, alkyl, aralkyl or aryl.

The reaction can be carried out in a suitable solvent such as dimethylsulfoxide, N,N-dimethylformamide or pyridine, in the presence or absence of a base such as sodium or potassium carbonate, or sodium or potassium hydroxide or the like inorganic base; triethylamine, pyridine or the like organic base; or sodium or potassium salt of the compound (II), and at a temperature of $-30°$–$100°$ C.

When the sodium or potassium salt of the compound (II) is to be selected for the starting material, the salt will be formed in situ by adding sodium or potassium hydride, in case of that anhydrous hydrous solvent such as dimethylsulfoxide, N,N-dimethylformamide or pyridine is selected and setting the temperature condition at $0°$–$30°$ C., for said reaction.

In either case of the reaction route (a) and (b), the derivative (I), wherein one of or both of the substituents Ra and Rb means a radical(s) other than hydrogen can be prepared and step-wise insertion of such radical(s) is possible, by controlling an amount of the compound of Ra-X or Rd-NCO, to be added.

In case of preparing medicines with use of the derivative according to the invention, there is no limitation in its form and thus it may be made into one for oral or none-oral administration, namely solid one such as tablets, pills, capsules, powder, granules, suppositories and others; or liquid one such as a solution, suspension, emulsion and others, with use of a conventional technique.

For preparing the solid type medicines, a starch, lactose, glucose, calcium phosphate, magnesium stearate, gum arabic or the like vehicle may be employed. If necessary, smoothening agent, binder, disintegration agent, coating agent, coloring agent and the like auxiliaries may be composed.

For preparing the liquid type medicines, a stabilizer, wetting agent, suspendizing agent, emulsifier, buffer, sterilizer or the like may be composed.

A dosing amount of the derivative for human depends on kind of the compound to be selected, condition of illness, age of a patient, form of the medicine and other variable factors but in case of an adult, 0.1 to 500 mg/day is preferable.

DETAILED DESCRIPTION OF PREFERRED EMBODIMENTS

The invention will now be further explained with reference to Examples for preparing the derivatives or compounds, Pharmacological Test Examples as well as Example for preparing medicine. Please note that in the Examples for preparing the compounds, reactions was carried out under argon, nitrogen or the like inert gas atmosphere, unless another condition shall be specifically referred to.

Examples 1–6

In DMF solution of (d)-6-fluoro-2,3-dihydro-2',5'-dioxo-spiro[4H-1-benzopyran-4,4'-imidazolidine]-2-carboxamide (3.50 g, 12.5 mmol), 60% sodium hydride (527 mg, 12.5 mmol) was added to stir the mixture for 1 hour at 10°–20° C. The reaction mixture was cooled to −10° C. and cyclohexylacetylchloride (2.01 g, 12.5 mmol) was added dropwise to stir the mixture for 2 hours at 0°–5° C. The resulting reaction mixture was poured into ice-water to obtain through a filtration formed crystals which was washed with water to afford desired (d)-1'-cyclohexylacetyl-6-fluoro-2,3-dihydro-2',5'-dioxo-spiro[4H-1-benzopyran-4,4'-imidazolidine]-2-carboxamide (4.45 g, 88%), (Example 1).

MS (m/z) spectrum: 403 (M+)
IR spectrum ($\nu_{max}^{KBr}$) cm$^{-1}$: 3475, 3325, 2920, 2850, 1805, 1760, 1715, 1685, 1495, 1350

| NMR spectrum (DMSO-d$_6$) δ ppm: | |
|---|---|
| 0.8–2.9 | (15H, m, CH$_2$ × 7 and —CH) |
| 4.98 | (1H, dd, J = 2.5 Hz, J = 12.2 Hz, C$_2$—H) |
| 6.9–7.3 | (3H, m, Ar—H) |
| 7.46, 7.71 | (2H, br.s, —NH$_2$) |
| 9.00 | (1H, s, —NH) |

UV spectrum ($\lambda_{max}$) nm: 216, 287

Following compounds were obtained through the procedures similar to the above (Example 1).

(d)-6-Fluoro-1'-propionyl-2',5'-dioxo-spiro[4H-1-benzopyran-4,4'-imidazolidine]-2-carboxamide (Example 2)

Yield: 29%
Melting point: 161° C.
MS (m/z) spectrum: 335 (M+)
IR spectrum ($\nu_{max}^{KBr}$) cm$^{-1}$: 3500, 3350, 1810, 1755, 1715, 1680, 1495, 1350, 1205

| NMR spectrum (DMSO-d$_6$) δ ppm: | |
|---|---|
| 0.9–1.2 | (3H, m, CH$_3$) |
| 2.04 | (1H, dd, J = 13.7 Hz, J = 12.6 Hz, C$_3$—H) |
| 2.7–3.1 | (2H, m, CH$_2$) |
| 2.70 | (1H, dd, J = 13.7 Hz, J = 2.4 Hz, C$_3$—H) |
| 2.9–3.1 | (2H, m, CH$_2$) |
| 4.98 | (1H, dd, J = 2.4 Hz, J = 12.6 Hz, C$_2$—H) |
| 7.0–7.2 | (3H, m, Ar—H) |
| 7.46, 7.71 | (2H, each s, —CONH$_2$) |
| 8.96 | (1H, s, —NH) |

UV spectrum ($\lambda_{max}$) nm: 218, 287

(d)-6-Fluoro-1'-methoxycarbonyl-2',5'-dioxo-spiro[4H-1-benzopyran-4,4'-imidazolidine]-2-carboxamide (Example 3)

Yield: 40%
Melting point: 183° C.
MS (m/z) spectrum: 337 (M+)
IR spectrum ($\nu_{max}^{KBr}$) cm$^{-1}$: 3425, 3320, 1815, 1775, 1725, 1675, 1495

| NMR spectrum (DMSO-d$_6$) δ ppm: | |
|---|---|
| 2.08 | (1H, dd, J = 2.4 Hz, J = 14.2 Hz, C$_3$—H) |
| 2.68 | (1H, dd, J = 12.6 Hz, J = 14.2 Hz, C$_3$—H) |
| 3.85 | (3H, s, CH$_3$) |
| 4.98 | (1H, dd, J = 2.4 Hz, J = 12.6 Hz, C$_2$—H) |
| 6.9–7.3 | (3H, m, Ar—H) |
| 9.02 | (1H, s, N$_3$'—H) |

UV spectrum ($\lambda_{max}$) nm: 221, 287

(d)-1'-Cyclohexyloxycarbonyl-6-fluoro-2,3-dihydro-2',5'-dioxo-spiro[4H-1-benzopyran-4,4'-imidazolidine]-2-carboxamide (Example 4)

Yield: 80%
Melting point: 154° C.
MS (m/z) spectrum: 405 (M+)
IR spectrum ($\nu_{max}^{KBr}$) cm$^{-1}$: 3450, 3360, 2940, 2860, 1810, 1775, 1685, 1495, 1260

| NMR spectrum (DMSO-d$_6$) δ ppm: | |
|---|---|
| 1.1–1.9 | (10H, m, CH$_2$ × 5) |
| 2.04 | (1H, dd, J = 12.7 Hz, J = 13.7 Hz, C$_3$—H) |
| 2.70 | (1H, dd, J = 2.4 Hz, J = 13.7 Hz, C$_3$—H) |
| 4.88 | (1H, m, —C—H) |
| 4.99 | (1H, dd, J = 2.4 Hz, J = 12.7 Hz, C$_2$—H) |
| 6.9–7.3 | (3H, m, Ar—H) |
| 7.72, 8.33 | (2H, each s, —CONH$_2$) |
| 9.00 | (1H, s, N$_3$'—H) |

UV spectrum ($\lambda_{max}$) nm: 220, 288

(d)-6-Fluoro-1'-phenoxycarbonyl-2,3-dihydro-2',5'-dioxo-spiro[4H-1-benzopyran-4,4'-imidazolidine]-2-carboxamide (Example 5)

Yield: 86%
Melting point: 221° C.
MS (m/z) spectrum: 399 (M+)
IR spectrum ($\nu_{max}^{KBr}$) cm$^{-1}$: 3475, 3350, 1815, 1780, 1730, 1680, 1490, 1260, 1195

| NMR spectrum (DMSO-d$_6$) δ ppm: | |
|---|---|
| 2.09 | (1H, dd, J = 12.7 Hz, J = 14.2 Hz, C$_3$—H) |
| 2.82 | (1H, dd, J = 2.4 Hz, J = 14.2 Hz, C$_3$—H) |
| 5.01 | (1H, dd, J = 2.4 Hz, J = 12.2 Hz, C$_2$—H) |
| 6.9–7.5 | (8H, m, Ar—H) |
| 7.52, 7.74 | (2H, each s, —CONH$_2$) |

| NMR spectrum (DMSO-d$_6$) δ ppm: | |
|---|---|
| 9.16 | (1H, s, N$_3$'—H) |

UV spectrum (λ$_{max}$) nm: 221, 288

(d)-6-Fluoro-1'-pivaloyloxymethyl-2,3-dihydro-2',5'-dioxo-spiro[4H-1-benzopyran-4,4'-imidazolidine]-2-carboxamide (Example 6)

Yield: 63%
Melting point: 104° C.
MS (m/z) spectrum: 393 (M$^+$)
IR spectrum ($\nu_{max}^{KBr}$) cm$^{-1}$: 3440, 3350, 2775, 1790, 1735, 1680, 1490, 1425, 1130

| NMR spectrum (DMSO-d$_6$) δ ppm: | |
|---|---|
| 1.12 | (9H, s, CH$_3$ × 3) |
| 2.11 | (1H, dd, J = 12.2 Hz, J = 13.2 Hz, C$_3$—H) |
| 2.51 | (1H, dd, J = 2.4 Hz, J = 13.2 Hz, C$_3$—H) |
| 5.02 | (1H, dd, J = 2.4 Hz, J = 12.2 Hz, C$_2$—H) |
| 5.41, 5.48 | (2H, each d, J = 10.3 Hz, —CH$_2$) |
| 7.50, 7.73 | (2H, each s, —CONH$_2$) |
| 8.92 | (1H, s, N$_3$'—H) |

UV spectrum (λ$_{max}$) nm: 224, 288

Example 7

In DMF solution of (d)-6-fluoro-2,3-dihydro-2',5'-dioxospiro[4H-1-benzopyran-4,4'-imidazolidine]-2-carboxamide (3.50 g, 12.5 mmol), triethylamine (1.80 g, 12.5 mmol) and phenylacetylchloride (1.94 g, 12.5 mmol) were added at −20° C. to stir the resulting mixture for 2 hours at 0°–5° C. The reaction mixture was poured into ice-water to obtain through a filtration formed crystals which was washed with water to afford desired (d)-6-fluoro-1'-phenylacetyl-2,3-dihydro-2',5'-dioxo-spiro[4H-1-benzopyran-4,4'-imidazolidine]-2-carboxamide (1.79 g, 36%).

Melting point: 166° C.
MS (m/z) spectrum: 397 (M$^+$)
IR spectrum ($\nu_{max}^{KBr}$) cm$^{-1}$: 3450, 2920, 2850, 1790, 1765, 1730, 1680, 1495, 1395, 1100

| NMR spectrum (DMSO-d$_6$) δ ppm: | |
|---|---|
| 2.10 | (1H, dd, J = 12.7 Hz, J = 13.6 Hz, C$_3$—H) |
| 2.62 | (1H, dd, J = 2.2 Hz, J = 13.6 Hz, C$_3$—H) |
| 3.93 | (2H, s, CH$_2$) |
| 5.02 | (1H, dd, J = 2.2 Hz, J = 12.7 Hz, C$_2$—H) |
| 6.9–7.4 | (8H, m, Ar—H) |
| 7.50, 7.74 | (2H, each s, —CONH$_2$) |
| 9.00 | (1H, s, N$_3$'—H) |

UV spectrum (λ$_{max}$) nm: 225, 276

Examples 8–12

In pyridine solution of (d)-6-fluoro-2,3-dihydro-2',5'-dioxo-spiro[4H-1-benzopyran-4,4'-imidazolidine]-2-carboxamide (3.50 g, 12.5 mmol), propionyl chloride (1.16 g, 12.5 mmol) was added dropwise at 0°–5° C. to stir the mixture for 5 hours at 10°–20° C. The reaction mixture was poured into ice-water to obtain through a filtration formed crystals which was washed with water to afford desired (d)-6-fluoro-3'-propionyl-2,3-dihydro-2',5'-dioxo-spiro[4H-1-benzopyran-4,4'-imidazolidine]-2-carboxamide (2.30 g, 55%), (Example 8).

Melting point: 275° C. (dec.)
MS (m/z) spectrum: 335 (M$^+$)
IR spectrum ($\nu_{max}^{KBr}$) cm$^{-1}$: 3480, 3350, 2745, 1785, 1730, 1715, 1665, 1495, 1370, 1215

| NMR spectrum (DMSO-d$_6$) δ ppm: | |
|---|---|
| 0.96 | (3H, t, J = 7.3 Hz, CH$_3$) |
| 2.50 | (1H, dd, J = 12.2 Hz, J = 12.2 Hz, C$_3$—H) |
| 2.68 | (1H, dd, J = 2.4 Hz, J = 12.2 Hz, C$_3$—H) |
| 2.92 | (2H, q, J = 7.3 Hz, CH$_2$) |
| 4.98 | (1H, dd, J = 2.4 Hz, J = 13.2 Hz, C$_2$—H) |
| 6.9–7.2 | (3H, m, Ar—H) |
| 7.46, 7.68 | (2H, each s, —CONH$_2$) |
| 11.96 | (1H, br.s, —N$_1$'—H) |

UV spectrum (λ$_{max}$) nm: 222, 287

Following compounds were obtained through the procedures similar to the above (Example 8).

(d)-6-Fluoro-3'-methoxycarbonyl-2',5'-dioxo-spiro[4H-1-benzopyran-4,4'-imidazolidine]-2-carboxamide (Example 9)

Yield: 20%
Melting point: 208° C.
MS (m/z) spectrum: 337 (M$^+$)
IR spectrum ($\nu_{max}^{KBr}$) cm$^{-1}$: 3480, 3350, 2750, 1800, 1740, 1665, 1495, 1370, 1330

| NMR spectrum (DMSO-d$_6$) δ ppm: | |
|---|---|
| 2.4–2.8 | (2H, m, C$_3$—H × 2) |
| 3.66 | (3H, s, CH$_3$) |
| 5.00 | (1H, dd, J = 2.4 Hz, J = 11.7 Hz, C$_2$—H) |
| 6.9–7.2 | (3H, m, Ar—H) |
| 7.48, 7.70 | (2H, each s, —CONH$_2$) |
| 11.95 | (1H, br.s, —NH) |

UV spectrum (λ$_{max}$) nm: 224, 288

(d)-3'-Cyclohexylacetyl-6-fluoro-2,3-dihydro-2',5'-dioxo-spiro[4H-1-benzopyran-4,4'-imidazolidine]-2-carboxamide (Example 10)

Yield: 40%
Melting point: 243° C. (dec.)
MS (m/z) spectrum: 403 (M$^+$)
IR spectrum ($\nu_{max}^{KBr}$) cm$^{-1}$: 3480, 3350, 2920, 2850, 1790, 1740, 1680, 1495, 1360

| NMR spectrum (DMSO-d$_6$) δ ppm: | |
|---|---|
| 0.9–1.8 | (10H, m, CH$_2$ × 5) |
| 2.4–2.9 | (4H, m, CH$_2$ × 2) |
| 3.9–4.1 | (1H, m, —C—H) |
| 4.97 | (1H, dd, J = 2.4 Hz, J = 12.7 Hz, C$_2$—H) |
| 6.9–7.2 | (3H, m, Ar—H) |
| 7.46, 7.68 | (2H, each s, —CONH$_2$) |
| 11.97 | (1H, s, N$_1$'—H) |

UV spectrum (λ$_{max}$) nm: 222, 288

(d)-3'-Cyclohexyloxycarbonyl-6-fluoro-2,3-dihydro-2',5'-dioxo-spiro[4H-1-benzopyran-4,4'-imidazolidine]-2-carboxamide (Example 11)

Yield: 30%
Melting point: 149° C.
MS (m/z) spectrum: 405 (M$^+$)
IR spectrum ($\nu_{max}^{KBr}$) cm$^{-1}$: 3480, 3350, 2935, 2860, 2750, 1815, 1755, 1680, 1495, 1360, 1340, 1305, 1110

| NMR spectrum (DMSO-d$_6$) δ ppm: | |
| --- | --- |
| 0.9–1.7 | (10H, m, CH$_2$ × 5) |
| 2.4–2.7 | (2H, m, C$_3$—H × 2) |
| 4.64 | (1H, m, —C—H) |
| 5.00 | (1H, dd, J = 2.4 Hz, J = 12.3 Hz, C$_2$× H) |
| 7.0–7.2 | (3H, m, Ar—H) |
| 7.47, 7.65 | (2H, each s, —CONH$_2$) |
| 11.95 | (1H, br.s, —NH) |

UV spectrum (λ$_{max}$) nm: 225, 287

(d)-6-Fluoro-3'-phenoxycarbonyl-2,3-dihydro-2',5'-dioxo-spiro[4H-1-benzopyran-4,4'-imidazolidine]-2-carboxamide (Example 12)

Yield: 17%
Melting point: 264° C. (dec.)
MS (m/z) spectrum: 399 (M+)
IR spectrum (ν$_{max}$$^{KBr}$) cm$^{-1}$: 3485, 3350, 3050, 2750, 1820, 1795, 1755, 1680, 1495, 1360, 1325, 1205

| NMR spectrum (DMSO-d$_6$) δ ppm: | |
| --- | --- |
| 2.5–2.8 | (2H, m, C$_3$—H × 2) |
| 4.9–5.1 | (1H, m, C$_2$—H) |
| 6.9–7.4 | (8H, m, Ar—H) |
| 7.48, 7.71 | (2H, each s, —CONH$_2$) |
| 12.16 | (1H, s, —NH) |

UV spectrum (λ$_{max}$) nm: 225, 288

Examples 13–15

In DMF solution of (d)-6-fluoro-2,3-dihydro-2',5'-dioxo-spiro[4H-1-benzopyran-4,4'-imidazolidine]-2carboxamide (3.50 g, 12.5 mmol), 60% sodium hydride (527 mg, 12.5 mmol) was added to stir the mixture for 1 hour at 10°–20° C.. The reaction mixture was cooled to −10° C. and ethyl isocyanate (0.89 g, 12.5 mmol) was added dropwise to stir the resulting mixture for 2 horus at the temperature of −10° C. The reaction mixture was poured into ice-water and pH of the solution was adjusted at 2 by concentrated hydrochloric acid to obtain through a filtration formed crystals of desired (d)-3'-ethylcarbamoyl-6-fluoro-2,3-dihydro-2',5'-dioxo-spiro[4H-1-benzopyran-4,4'-imidazolidine]-2-carboxamide (2.99 g, 68%), (Example 13).

Melting point: 248° C. (dec.)
MS (m/z) spectrum: 350 (M+)
IR spectrum (ν$_{max}$$^{KBr}$) cm$^{-1}$: 3475, 3350, 2730, 1775, 1735, 1540, 1495, 1380

| NMR spectrum (DMSO-d$_6$) δ ppm: | |
| --- | --- |
| 1.04 | (3H, t, J = 6.8 Hz, CH$_3$) |
| 2.52 | (1H, dd, J = 2.4 Hz, J = 13.7 Hz, C$_3$—H) |
| 2.86 | (1H, dd, J = 12.7 Hz, J = 13.7 Hz, C$_3$—H) |
| 3.13 | (2H, m, CH$_2$) |
| 5.03 | (1H, dd, J = 2.4 Hz, J = 12.7 Hz, C$_2$—H) |
| 6.9–7.2 | (3H, m, Ar—H) |
| 7.47, 7.68 | (2H, each s, —CONH$_2$) |
| 8.06 | (1H, t, J = 5.9 Hz, —NH) |
| 12.0 | (1H, s, —N$_1$'—H) |

UV spectrum (λ$_{max}$) nm: 225, 288
Following compounds were obtained through the procedures similar to the above (Example 13).

(d)-3'-Cyclohexylcarbamoyl-6-fluoro-2,3-dihydro-2',5'-dioxo-spiro[4H-1-benzopyran-4,4'-imidazolidine]-2-carboxamide (Example 14)

Yield: 87%
Melting point: 221° C.
MS (m/z) spectrum: 404 (M+)
IR spectrum (ν$_{max}$$^{KBr}$) cm$^{-1}$: 3400, 3325, 3200, 2930, 2850, 2740, 1785, 1735, 1690, 1675, 1550, 1495, 1375

| NMR spectrum (DMSO-d$_6$) δ ppm: | |
| --- | --- |
| 1.1–1.9 | (11H, m, CH$_2$ × 5 and —C—H) |
| 2.50 | (1H, dd, J = 2.4 Hz, J = 14.2 Hz, C$_3$—H) |
| 2.83 | (1H, dd, J = 12.5 Hz, J = 14.2 Hz, C$_3$—H) |
| 4.98 | (1H, dd, J = 2.4 Hz, J = 12.5 Hz, C$_2$—H) |
| 6.9–7.2 | (3H, m, Ar—H) |
| 7.66, 7.67 | (2H, each s, —CONH$_2$) |
| 7.99 | (1H, d, J = 7.8 Hz, —NH) |

UV spectrum (λ$_{max}$) nm: 227, 288

(d)-6-Fluoro-3'-phenylcarbamoyl-2,3-dihydro-2',5'-dioxospiro[4H-1-benzopyran-4,4'-imidazolidine]-2-carboxamide (Example 15)

Yield: 85%
Melting point: 237° C.
MS (m/z) spectrum: 398 (M+)
IR spectrum (ν$_{max}$$^{KBr}$) cm$^{-1}$: 3430, 3310, 3050, 2740, 1780, 1740, 1680, 1600, 1550, 1495, 1375, 1210

| NMR spectrum (DMSO-d$_6$) δ ppm: | |
| --- | --- |
| 2.63 | (1H, dd, J = 2.4 Hz, J = 13.7 Hz, C$_3$—H) |
| 2.89 | (1H, dd, J = 12.7 Hz, J = 13.7 Hz, C$_3$—H) |
| 5.03 | (1H, dd, J = 2.4 Hz, J = 12.7 Hz, C$_2$—H) |
| 7.0–7.5 | (8H, m, Ar—H) |
| 7.49, 7.77 | (2H, each s, —CONH$_2$) |
| 10.16 | (1H, s, —NH) |
| 12.35 | (1H, s, —NH) |

UV spectrum (λ$_{max}$) nm: 255, 286

Examples 16

In DMF solution of (d)-6-fluoro-2,3-dihydro-2',5'-dioxospiro[4H-1-benzopyran-4,4'-imidazolidine]-2-carboxamide (3.50 g, 12.5 mmol), 60% sodium hydride (527 mg, 12.5 mmol) was added to stir the mixture for 1 hour at 10°−20° C. The reaction mixture was cooled to −20° C. and p-toluenesulfonyl chloride (2.38 g, 12.5 mmol) was added to stir the mixture for 2 hours at the temperature of 0°–5° C. The reaction mixture was poured into ice-water to obtain through a filtration formed crystals which were chromatographed (eluent: 10% methanol/dichloro-methane) to afford desired (d)-6-fluoro-1'-(p-toluenesulfonyl)-2,3-dihydro-2',5'-dioxo-spiro[4H-1-benzopyran-4,4'-imidazolidine]-2-carboxamide (Compound A), (0.80 g, 14.6%) and (d)-6-fluoro-1',3'-bis-p-(toluenesulfonyl)-2,3-dihydro-2',5'-dioxo-spiro[4H-1-benzopyran-4,4'-imidazolidine]-2-carboxamide (Compound B), (1.89 g, 26.9%).

Compound A

Melting point: 171° C. (dec.)
MS (m/z) spectrum: 433 (M+)

IR spectrum ($\nu_{max}^{KBr}$) cm$^{-1}$: 3610, 3360, 1805, 1755, 1680, 1595, 1495, 1385, 1325, 1190, 1175, 1090, 570, 545

| NMR spectrum (DMSO-d$_6$) δ ppm: | |
|---|---|
| 2.00 | (1H, dd, J = 2.4 Hz, J = 14.2 Hz, C$_3$—H) |
| 2.49 | (1H, dd, J = 12.2 Hz, J = 14.2 Hz, C$_3$—H) |
| 3.25 | (3H, s, CH$_3$) |
| 4.92 | (1H, dd, J = 2.4 Hz, J = 12.2 Hz, C$_2$—H) |
| 6.5–7.3 | (3H, m, Ar—H) |
| 7.47, 7.74 | (2H, each s, —CONH$_2$) |
| 7.94, 7.90 | (4H, each d, J = 7.8 Hz, Ar—H) |
| 9.28 | (1H, s, —N$_3$'—H) |

UV spectrum ($\lambda_{max}$) nm: 230, 283

Compound B

Melting point: 191° C.
MS (m/z) spectrum: 587 (M+)
IR spectrum ($\nu_{max}^{KBr}$) cm$^{-1}$: 3500, 3375, 2925, 2850, 1805, 1755, 1695, 1595, 1495, 1405, 1280, 1215, 1200, 1175, 1145, 1085, 665, 580, 565, 545

| NMR spectrum (DMSO-d$_6$) δ ppm: | |
|---|---|
| 1.98 | (6H, s, CH$_3$ × 2) |
| 2.49 | (1H, dd, J = 2.4 Hz, J = 14.2 Hz, C$_3$—H) |
| 2.74 | (1H, dd, J = 12.7 Hz, J = 14.2 Hz, C$_3$—H) |
| 4.98 | (1H, dd, J = 2.4 Hz, J = 12.7 Hz, C$_2$—H) |
| 6.5–8.0 | (13H, m, Ar—H and —CONH$_2$) |

UV spectrum ($\lambda_{max}$) nm: 234, 285

Examples 17

In DMF solution of (d)-6-fluoro-2,3-dihydro-2',5'-dioxospiro[4H-1-benzopyran-4,4'-imidazolidine]-2-carboxamide (3.50 g, 12.5 mmol), triethylamine (5.10 g, 50.3 mmol) and hydrochloride of nocotinoylchloride were added at a temperature of 0°–5° C. to stir the mixture for 5 hours at the temperature of 0°–5° C. The reaction mixture was poured into ice-water to obtain through a filtration formed crystals which were washed with water to afford desired (d)-6-fluoro-3'-nicotinoyl-2,3-dihydro-2',3'-dioxospiro[4H-1-benzopyran-4,4'-imidazolidine]-2-carboxamide (3.50 g, 73%).

Melting point: 250° C. (dec.)
MS (m/z) spectrum: 384 (M+)
IR spectrum ($\nu_{max}^{KBr}$) cm$^{-1}$: 3450, 3320, 3280, 2700, 1780, 1730, 1660, 1565, 1485, 1355, 1320, 1195

| NMR spectrum (DMSO-d$_6$) δ ppm: | |
|---|---|
| 2.70 | (1H, dd, J = 2.5 Hz, J = 13.7 Hz, C$_3$—H) |
| 2.83 | (1H, dd, J = 12.2 Hz, J = 13.7 Hz, C$_3$—H) |
| 4.99 | (1H, dd, J = 2.5 Hz, J = 12.2 Hz, C$_2$—H) |
| 7.0–7.2 | (4H, m, Ar—H and Py–H) |
| 7.53, 7.76 | (2H, each s, —CONH$_2$) |
| 8.10 | (1H, m, Py—H) |
| 8.70 | (1H, dd, J = 1.5 Hz, J = 4.9 Hz, Py—H) |
| 8.88 | (1H, d, J = 1.5 Hz, Py—H) |
| 12.18 | (1H, br., N'—H) |

UV spectrum ($\lambda_{max}$) nm: 230, 280

Pharmacological Test Example 1

Ameriorative effect on polyol accumulation in sciatic nerve of galactosemic rats Some compounds according to the invention as well as a control compound of "Sorbinil", namely dl-6-fluoro-2,3-dihydrospiro[4H-1-benzopyran-4,4'-imidazolidine]-2',5'-dione were orally and forcedly administered to S.D. male rats (weight of about 50 g) at a dose of 10 mg/kg once a day for a testing time period of 8 days, under giving 30% galactose diet. One day after the final administration (after lapsed 24 hours from the first administration), sciatic nerves of the rats were removed for determination of galactitol accumulated therein.

Results are shown in following Table 1. As apparently seen therefrom, the compounds according to the invention have an excellent action of inhibiting an accumulation of galactitose.

TABLE 1

| Compounds | Inhibition (%) |
|---|---|
| Test compound | |
| Example 3 | 83 |
| 6 | 79 |
| 16-A | 56 |
| Control | |
| dl-Sorbinil | 44 |

Pharmacological Test Example 2

Inhibition of aldose reductase activity

Some compounds according to the invention as well as a control compound of "Sorbinil", namely dl-6-fluoro-2,3-dihydrospiro[4H-1-benzopyran-4,4'-imidazolidine]-2',5'-dione were tested to evaluate their ability on reduction or inhibition of aldose reductase activity, in accordance with the procedure proposed by Kador and Sharpless ["Biophysical Chemistry", Vol. 8, page 81 (1978)].

Using water-soluble extracts of crystalline lenses extracted from tested rats, the inhibition of these compounds was determined. Results are shown in following Table 2, wherein a value of "IC$_{50}$" represents the concentration of inhibitor which gives 50% inhibition. As apparently seen from the Table, the compounds according to the invention show an excellent inhibition activity to aldose reductase.

TABLE 2

| Compounds | IC$_{50}$ (M) |
|---|---|
| Test compound | |
| Example 3 | 4.5 × 10$^{-8}$ |
| 6 | 1.0 × 10$^{-4}$ |
| 16-A | 1.0 × 10$^{-4}$ |
| Control | |
| dl-Sorbinil | 4.0 × 10$^{-6}$ |

Medicine Preparation Example (Tablets)

To a mixture of (d)-6-fluoro-1'-pivaloyloxymethyl-2,3-dihydro-2',5'-dioxo-spiro[4H-1-benzopyran-4,4'-imidazolidine]-2-carboxamide as an active ingredient (50 parts by weight, Example 6), lactose (27 parts by weight) and corn starch (20 parts by weight), a paste of corn starch (2 parts by weight) and water (40 parts by weight) was added to mix wholly. The resulting mixture was passed through 15 mesh screen (a standard sieve according to the Japanese Industrial Standards), dried at 60° C., and passed through 20 mesh screen according to JIS to prepare fine granules.

To the granules, 1 part by weight of magnesium stearate was added to sufficiently mix the same. The resulting mixture was tabletted in a conventional manner to prepare tablets which are different in size to contain 10, 20, 50 and 100 mg as the active ingredient.

What is claimed is:

1. A (d)-6-fluoro-2,3-dihydro-2',5'-dioxo-spiro[4H-1-benzopyran-4,4'-imidazolidine]-2-carboxamide compound of the formula

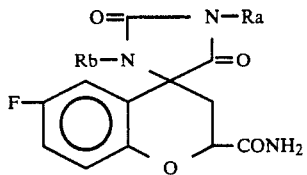

wherein Ra and Rb are the same or different, each being hydrogen, alkanoyl, cyclohexanoyl, aroyl, furoyl, nicotinoyl, alkoxycarbonyl, aralkoxycarbonyl, aryloxycarbonyl, N-alkylcarbamoyl, N,N-dialkylcarbamoyl, N-aralkylcarbamoyl, alkoxyalkyl, 1-($C_1$–$C_{10}$alkanoyl)alkyl, alkylmercapto, arylmercapto, alkylsulfinyl, arylsulfinyl, alkylsulfonyl or arylsulfonyl, wherein aroyl and aryl may be substituted by chloro, methoxy or methyl, with the proviso that both of Ra and Rb are not concurrently hydrogen.

2. A pharmaceutical composition for the treatment of chronic complications due to diabetes, which comprises an effective amount for such treatment of a (d)-6-fluoro-2,3-dihydro-2',5'-dioxo-spiro[4H-1-benzopyran-4,4'-imidazolidine]-2-carboxamide compound of the formula

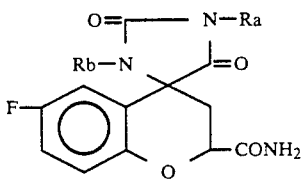

wherein Ra and Rb are the same or different, each being hydrogen, alkanoyl, cyclohexanoyl, aroyl, furoyl, nicotinoyl alkoxycarbonyl, aralkoxycarbonyl, aryloxycarbonyl, N-alkylcarbamoyl, N,N-dialkylcarbamoyl, N-aralkylcarbamoyl, alkoxyalkyl, 1-($C_1$–$C_{10}$ alkanoyl)alkyl, alkylmercapto, arylmercapto, alkylsulfinyl, arylsulfinyl, alkylsulfonyl or arylsulfonyl, wherein aroyl and aryl may be substituted by chloro, methoxy or methyl, with the proviso that both of Ra and Rb are not concurrently hydrogen; and a pharmaceutically acceptable carrier therefor.

3. A compound as claimed in claim 1 selected from the group consisting of (d)-1'-Cyclohexylacetyl-6-fluoro-2,3-dihydro-2',5'-dioxospiro [4H-1-benzopyran-4,4'-imidazolidine]-2-carboxamide; (d)-6-Fluoro-1'-propionyl-2',5'-dioxo-spiro[4H-1-benzo-pyran-4,4'-imidazolidine]-2-carboxamide;

(d)-6-Fluoro-1'-methoxycarbonyl-2',5'-dioxo-spiro[4H-1-benzopyran-4,4'-imidazolidine]-2-carboxamide;

(d)-1'-Cyclohexyloxycarbonyl-6-fluoro-2,3-dihydro-2',5'-dioxo-spiro[4H-1-benzopyran-4,4'-imidazolidine]-2-carboxamide;

(d)-6-Fluoro-1'-phenoxycarbonyl-2,3-dihydro-2',5'-dioxo-spiro[4H-1-benzopyran-4,4'-imidazolidine]-2-carboxamide;

(d)-6-Fluoro-1'-pivaloyloxymethyl-2,3-dihydro-2',5'-dioxo-spiro[4H-1-benzopyran-4,4'-imidazolidine]-2-carboxamide;

(d)-6-Fluoro-1'-phenylacetyl-2,3-dihydro-2',5'-dioxo-spiro[4H-1-benzopyran-4,4'-imidazolidine]-2-carboxamide;

(d)-6-Fluoro-3'-propionyl-2,3-dihydro-2',5'-dioxo-spiro[4H-1-benzopyran-4,4'-imidazolidine]-2-carboxamide;

(d)-6-Fluoro-3'-methoxycarbonyl-2',5'-dioxo-spiro[4H-1-benzopyran-4,4'-imidazolidine]-2-carboxamide;

(d)-3'-Cycrohexylacetyl-6-fluoro-2,3-dihydro-2',5'-dioxo-spiro[4H-1-benzopyran-4,4'-imidazolidine]-2-carboxamide;

(d)-3'-Cyclohexyloxycarbonyl-6-fluoro-2,3-dihydro-2',5'-dioxo-spiro[4H-1-benzopyran-4,4'-imidazolidine]-2-carboxamide;

(d)-6-Fluoro-3'-phenoxycarbonyl-2,3-dihydro-2',5'-dioxo-spiro[4H-1-benzopyran-4,4'-imidazolidine]-2-carboxamide;

(d)-3'-Ethylcarbamoyl-6-fluoro-2,3-dihydro-2',5'-dioxo-spiro[4H-1-benzopyran-4,4'-imidazolidine]-2-carboxamide;

(d)-3'-Cyclohexylcarbamoyl-6-fluoro-2,3-dihydro-2',5'-dioxo-spiro[4H-1-benzopyran-4,4'-imidazolidine]-2-carboxamide;

(d)-6-Fluoro-3'-phenylcarbamoyl-2,3-dihydro-2',5'-dioxo-spiro[4H-1-benzopyran-4,4'-imidazolidine]-2-carboxamide;

(d)-6-Fluoro-1'-p-(toluenesulfonyl)-2,3-dihydro-2',5'-dioxo-spiro[4H-1-benzopyran-4,4'-imidazolidine]-2-carboxamide;

(d)-6-Fluoro-1',3'-bis-p-(toluenesulfonyl)-2,3-dihydro-2',5'-dioxo-spiro[4H-1-benzopyran-4,4'-imidazolidine]-2-carboxamide; and (d)-6-Fluoro-3'-nicotinoyl-2,3-dihydro-2',5'-dioxo-spiro[4H-1-benzopyran-4,4'-imidazolidine]-2-carboxamide.

* * * * *

UNITED STATES PATENT AND TRADEMARK OFFICE
CERTIFICATE OF CORRECTION

PATENT NO. : 5,036,080

DATED : July 30, 1991

INVENTOR(S) : Masayasu KURONO et al

It is certified that error appears in the above-identified patent and that said Letters Patent is hereby corrected as shown below:

On the title page, Item [54], third line, "IMIDAZOLIDE" should read -- IMIDAZOLIDINE --.

Signed and Sealed this

Fifth Day of January, 1993

Attest:

DOUGLAS B. COMER

Attesting Officer

Acting Commissioner of Patents and Trademarks